United States Patent [19]
Globig et al.

[11] Patent Number: 5,153,672
[45] Date of Patent: Oct. 6, 1992

[54] HIGH BANDWIDTH VAPOR DENSITY DIAGNOSTIC SYSTEM

[75] Inventors: Michael A. Globig, Antioch; Thomas W. Story, Oakley, both of Calif.

[73] Assignee: The United States of America as represented by the United States Department of Energy, Washington, D.C.

[21] Appl. No.: 337,981

[22] Filed: Apr. 14, 1989

[51] Int. Cl.$^5$ .................. G01J 3/30; G01N 21/00; H01J 27/00

[52] U.S. Cl. .................. 356/311; 250/423 P; 250/425; 356/300; 356/432; 356/436

[58] Field of Search ............ 356/72, 73, 311, 300, 356/432, 436; 250/423 P, 425

[56] References Cited
U.S. PATENT DOCUMENTS
4,817,101 3/1989 Wyeth et al. ............ 356/349

Primary Examiner—Stephen C. Buczinski
Attorney, Agent, or Firm—Miguel A. Valdes; Roger S. Gaither; William R. Moser

[57] ABSTRACT

A high bandwidth vapor density diagnostic system for measuring the density of an atomic vapor during one or more photoionization events. The system translates the measurements from a low frequency region to a high frequency, relatively noise-free region in the spectrum to provide improved signal to noise ratio.

14 Claims, 5 Drawing Sheets

HIGH BANDWIDTH VAPOR DENSITY DIAGNOSTIC SYSTEM

FIELD OF THE INVENTION

The United States Government has rights in this invention pursuant to Contract No. W-7405-ENG-48 between the United States Department of Energy and the University of California for operation under Lawrence Livermore National Laboratory.

BACKGROUND OF THE INVENTION

The present invention relates to a high bandwidth vapor density diagnostic system for use in an atomic vapor laser isotope separation (AVLIS) process.

In an AVLIS process, an atomic vapor is photoionized by one or more laser beams to provide a separation of a desired isotope. As an example, in a uranium vapor comprising U235 and U238 isotopes, the uranium vapor is photoionized by appropriate laser beams to separate the U235 isotopes from the U238 isotopes. An AVLIS process can be utilized in other environments in which is it desired to separate particular isotopes of th specific atomic vapor.

Standard vapor density diagnostic systems in an AVLIS process scan a ring-dye laser over an atomic transition and calculate the density from the transmission signal approximately every four seconds. This technique returns a vapor density value that has to be averaged over thousands of photoionization events. It would be desirable to provide an improved vapor density diagnostic system that can measure vapor density variations during a single photoionization event.

SUMMARY OF THE INVENTION

It is an object of the present invention to provide an improved vapor density diagnostic system for use in an AVLIS process. It is a more particular object of the present invention to provide a high bandwidth vapor density diagnostic system.

In one preferred embodiment, the high bandwidth atomic vapor density diagnostic system according to the present invention includes means for amplitude modulating a high bandwidth laser beam, means for propagating the modulated laser beam through an atomic vapor during one or more photoionization events, means for detecting the propagated laser beam, and lock-in amplifier means for removing pickup noise from the detected signal.

The system can further include means for digitizing the detected signal and means for processing the digitized signal to process or measure the vapor density variation during one or more of the photoionization events.

Additional objects, advantages and novel features of the present invention will be set forth in part in the description which follows and in part become apparent to those skilled in the art upon examination of the following, or may be learned by practice of the invention. The objects and advantages of the invention may be realized and attained by means of the instrumentalities and combinations which are pointed out in the appended claims.

BRIEF DESCRIPTION OF THE DRAWINGS

The accompanying drawings which are incorporated in and form a part of this specification illustrate an embodiment of the invention and, together with the description, serve to explain the principles of the invention.

DETAILED DESCRIPTION OF THE DRAWINGS

Reference will now be made in detail to the preferred embodiment of the invention, an example of which is illustrated in the accompanying drawings. While the invention will be described in conjunction with the preferred embodiment, it will be understood that it is not intended to limit the invention to that embodiment. On the contrary, it is intended to cover alternatives, modifications and equivalents as may be included within the spirit and scope of the invention as defined by the appended claims.

As previously described, the standard approach for a vapor density diagnostic system scan a ring-dye laser over an atomic transition and calculate a density from the transmission signal approximately every four seconds. That technique returns a vapor density value that has been averaged over thousands of photoionization events. It would be desirable to provide an improved diagnostic system to measure vapor density variation during a single photoionization event (or during one or more photoionization events).

In such an approach, the new diagnostic system must have a time bandwidth of around 0.5 to 1.0 MHz. These new specifications indicate an 8 million times increase in speed over old diagnostic techniques.

The new system is similar to an existing diagnostic system at the system block level approach. The present invention increases the bandwidth (speed) of some of the existing system's functions. Laser light is amplitude modulated or chopped, except the rate has increased from 1-5 KHz to 32 MHz. The light is synchronously detected by a lock-in amplifier which can operate at 32 MHz. Prior systems are not capable of such an approach.

Figure 1:
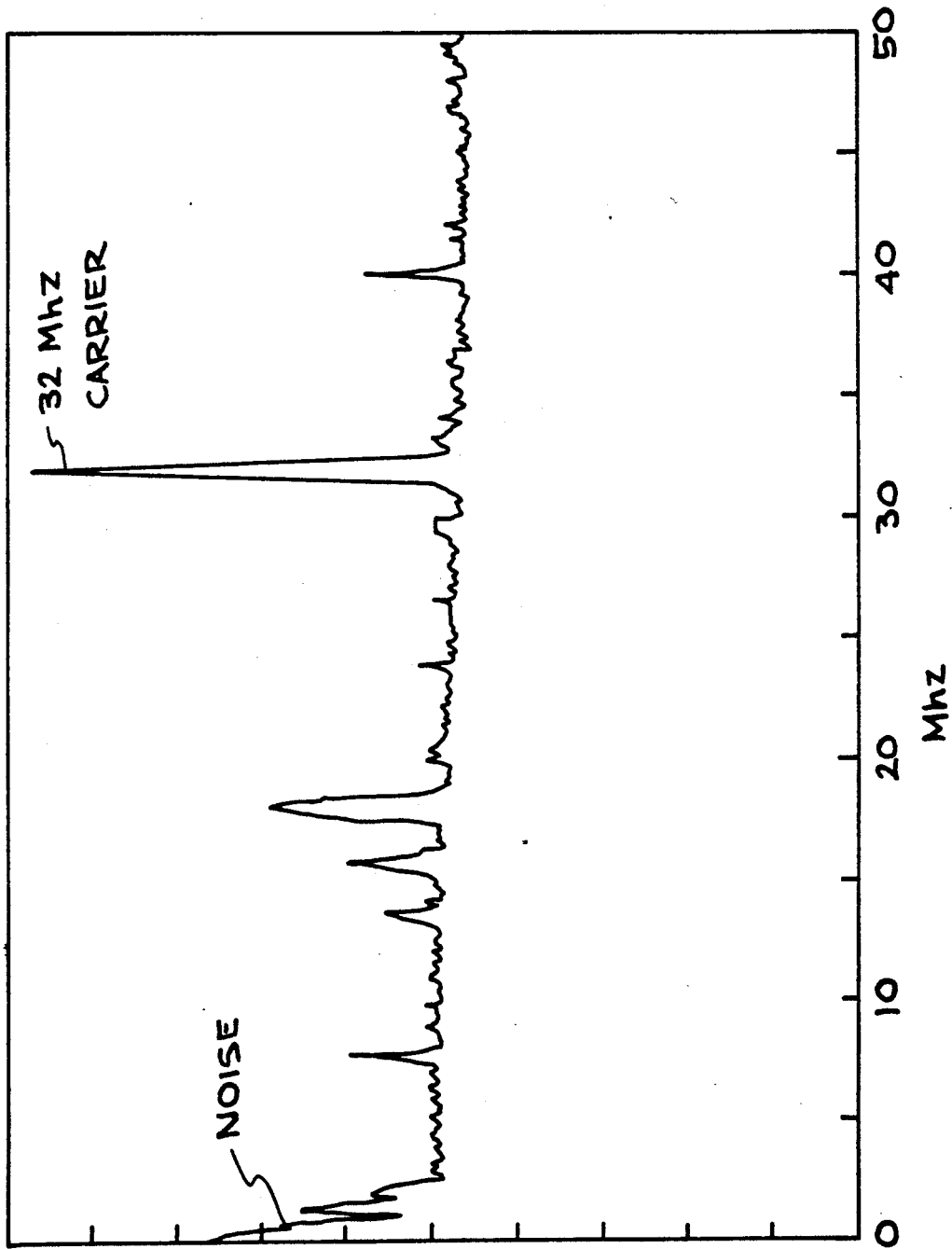
FIG. 1 depicts a spectrum analyzer scan which shows improved signal to noise ratio obtained in accordance with the present invention.

The present invention provides a significant advantage in increased signal to noise ratio. FIG. 1 depicts a spectrum analyzer scan of the detector of the present invention depicted in FIG. 2.

In FIG. 1, the region around the 32 MHz carrier has relatively low noise compared to the 0 to 2 MHz region. Noise in the lower region is approximately 20 db higher and can be contributed to 1/F noise, 60 Hz and 120 Hz from power supplies, DC drift and possibly video signal pickup.

By translating the measurement to a relatively noise-free region of the spectrum (such as the 32 MHz carrier region), signal to noise ratio can It is believed that the present invention increases the signal to noise ratio by at least 20 db.

Figure 2:
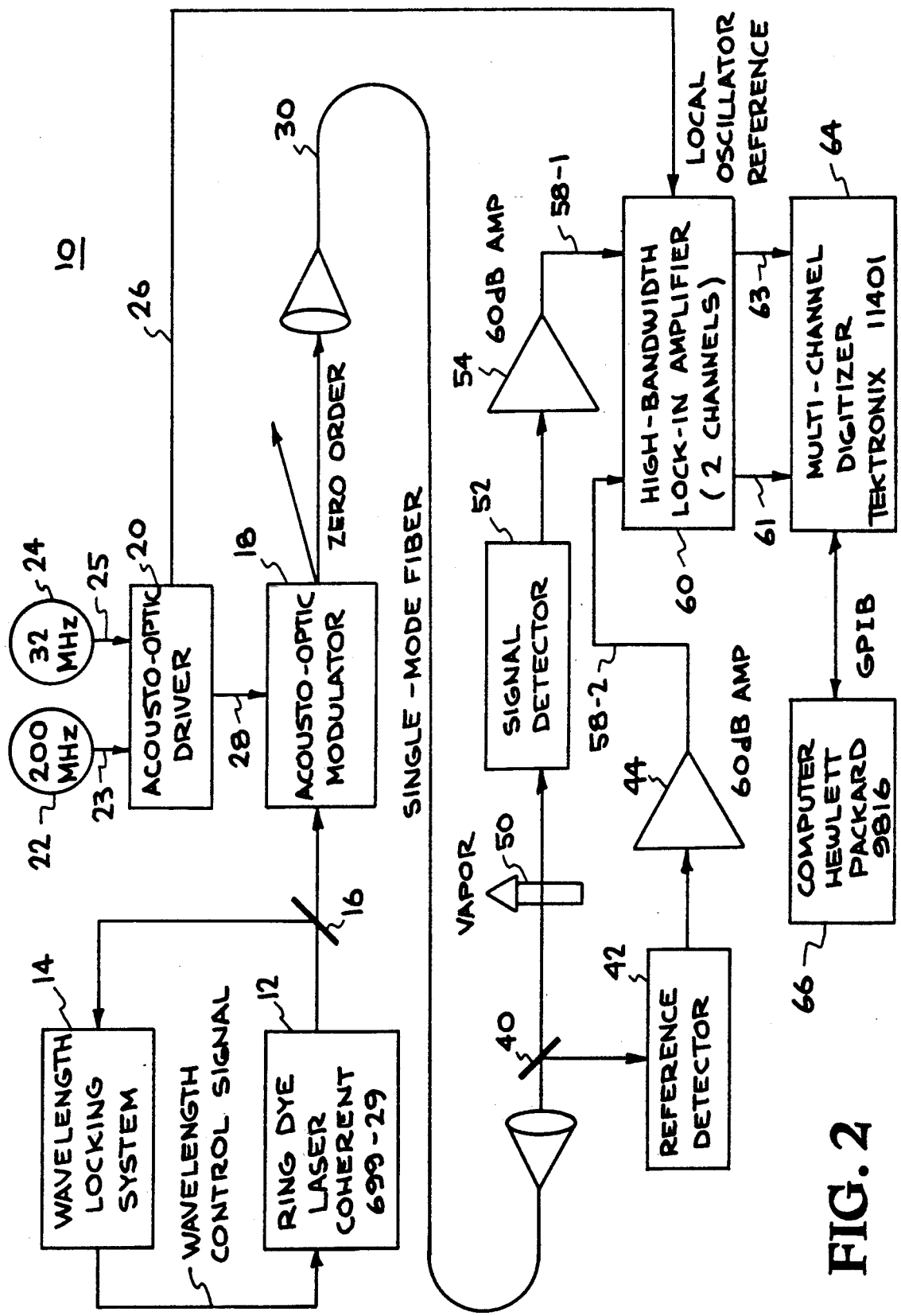
FIG. 2 depicts a block diagram of a high bandwidth vapor density diagnostic system according to the present invention.

FIG. 2 depicts a block diagram of a high bandwidth vapor density diagnostic system according to the present invention.

In FIG. 2, a ring-dye laser 12 is locked with an offset by wavelength locking system 14 to a molecular iodine atomic transition. As mentioned above, existing diagnostic systems are wavelength scanned, while the present invention is locked to the peak absorption of an atomic transition (a subject not covered by the scope of the present invention).

Referring again to FIG. 2, the light from laser 12 is amplitude modulated or chopped by an acousto-optic modulator 18. Because of the high modulation frequency, standard mechanical choppers are too slow, and an acousto-optic modulator driver 20 is necessary.

Figure 3A:
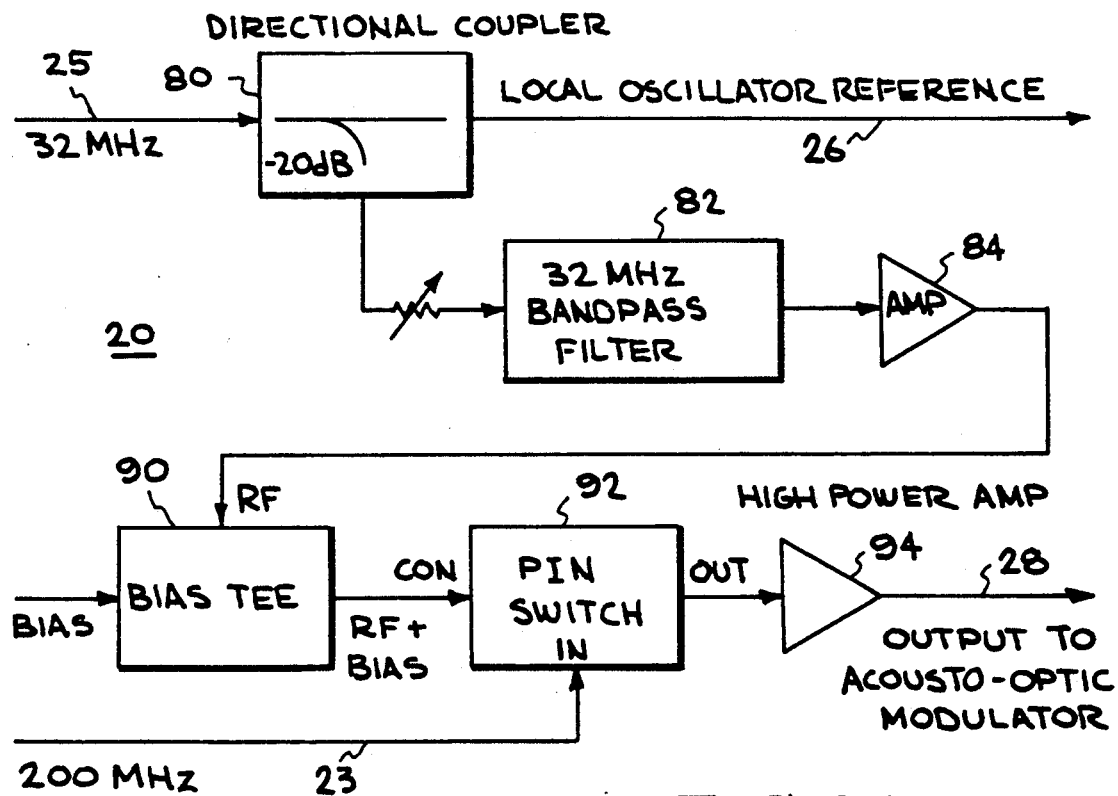
FIG. 3A depicts a block diagram of an acoustic optic driver which forms a portion of FIG. 2
Figure 3B:
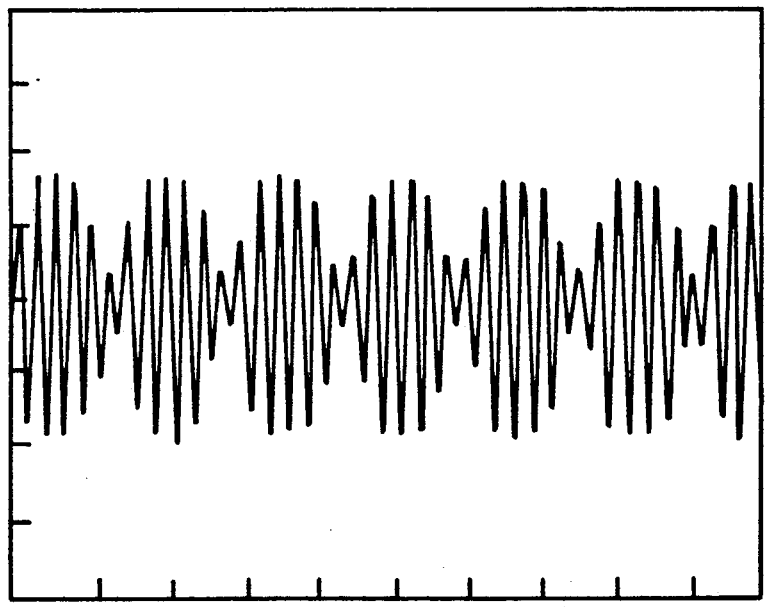
FIG. 3B depicts a waveform representation output of the acousto-optic driver.

FIG. 3 shows a more detailed diagram of the acousto-optic driver 20 of FIG. 2. In FIG. 3A, a 32 MHz signal on lead 25 is input to a directional coupler 80 through a 32 MHz bandpass filter 82 and amplifier 84 to a bias tee 90. FIG. 3B depicts a representation of the output of high power amp 94 to the acousto-optic modulator.

An acousto-optic carrier frequency of 200 MHz on lead 23 is amplitude modulated by the 32 MHz signal in switch 92 to form a sinusoidally modulated carrier signal at 32 MHz. This signal is output on lead 28 to the acoustic optic modulator 18 of FIG. 2.

Referring again to FIG. 2, the light from laser 12 is modulated with the sinusoidal signal from acousto-optic driver 20 in modulator 18. Thus, the laser beam is effectively sinusoidally modulated.

The output of modulator 18 is a modulated light beam which is captured by the single mode optical fiber cable 30 and transported to a suitable vapor source, which could be at a remote location.

The modulated laser beam is sampled by reference detector 42 which is amplified by 60 db amplifier 44 for input to a high bandwidth lock-in amplifier 60 which could be remotely located.

Reference detector 42 is needed to ratio out laser light amplitude fluctuations caused by several sources.

The balance of the light is propagated through beam splitter 40 through an atomic vapor 50 to a signal detector 52. Low power levels are necessary for the light propagating through vapor 50 to avoid optically pumping the vapor or, in other words, avoid having the measuring diagnostic system change the vapor density. Due to low power levels, 60 db of amplification follows signal detector 52 in amplifier 54.

It will be understood that the present invention does not optically pump an atomic vapor. Rather, as is known in an AVLIS process, the photoionization occurs by a separate photoionization beam, and the purpose of the present invention is to provide a vapor density diagnostic system.

After amplification of the detected signals, the signals are synchronously detected by a high bandwidth lock-in amplifier 60, as depicted in FIG. 2.

Figure 4:
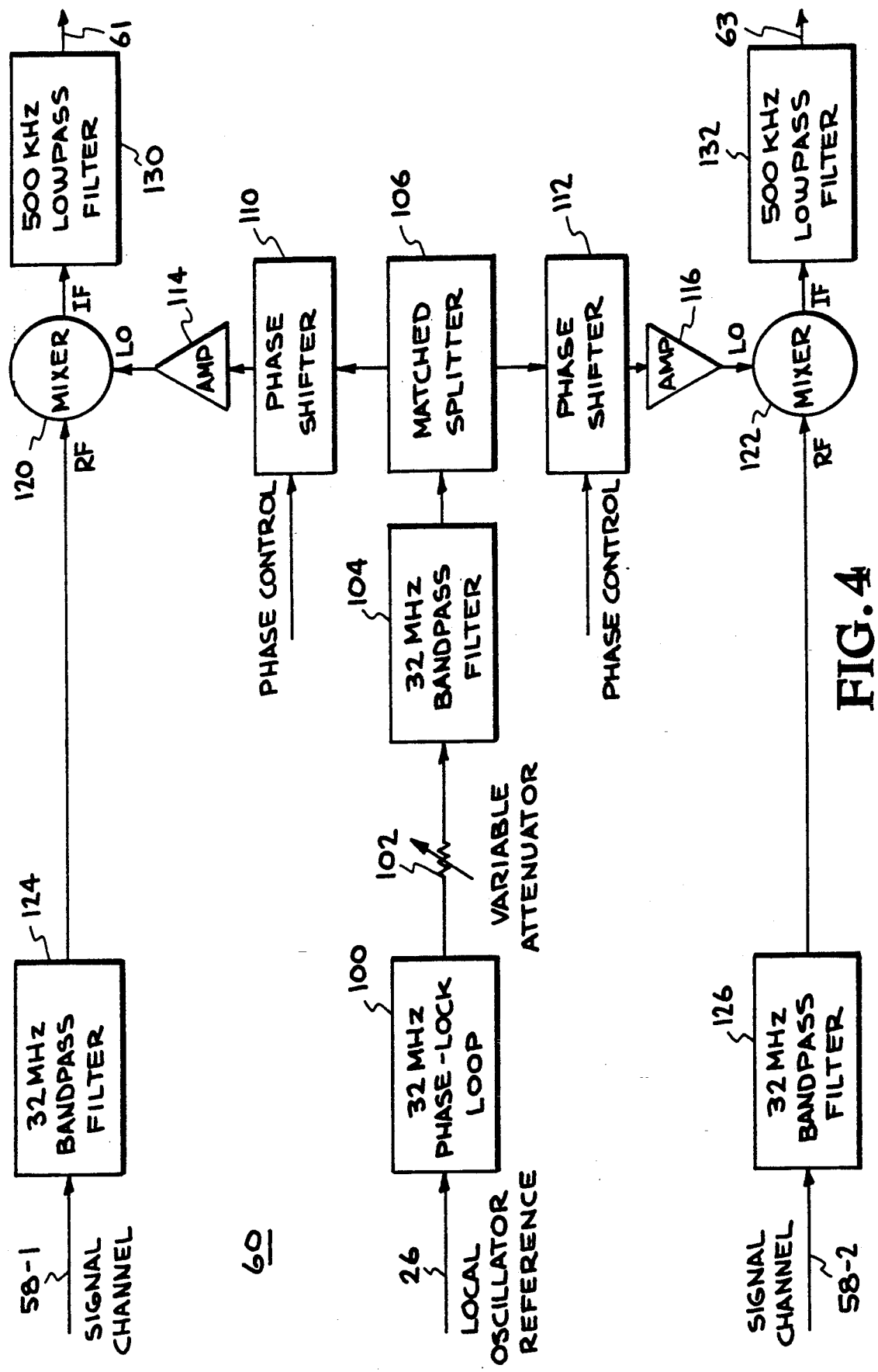
FIG. 4 depicts a block diagram of a high bandwidth lock-in amplifier which forms a portion of FIG. 2.

FIG. 4 depicts a more detailed block diagram of the high bandwidth lock-in amplifier 60 of FIG. 2. In FIG. 4, the lock-in amplifier removes out of band and out of phase pickup noise from the detected signal. The lock-in amplifier ca be placed in a convenient location remote from the vapor source 50 of FIG. 2. The lock-in amplifier 60 is designed using RF components to accommodate the higher frequency/wider bandwidth measurements.

In FIG. 4, the local oscillator reference signal on lead 60 is input to a 32 MHz phase locked loop (PLL) 100. PLL 100 is used to stabilize any long term amplitude drifts and to remove any noise pickup by the long local oscillator cable 26.

Following PLL 100, an attenuator 102 sets the proper amplitude level, and 32 MHz bandpass filter 104 removes any PLL harmonics. The reference signal of FIG. 2 is split to accommodate two channels and next phase shifted to peak the lock-in amplifier's output signal.

After amplifying in amplifiers 114, 116, the local oscillator reference signal is input to the LO port of a double balanced mixer (or phase detector) 120, 122.

The signal from the photodetector on leads 58-1 and 58-2 are sent through bandpass filters 124, 126 (32 MHz center frequency and 2 MHz pass band) to remove any out of band noise. Next, the photodetector signal is mixed with the LO reference signal and the IF output of mixers 120, 122 are filtered by 0.5 to 1.0 MHz low pass filters 130, 132.

Low pass filters 130, 132 are needed to remove any 32 MHz leakage through the mixers 120, 122 and to frequency band limit the signal to avoid high frequency aliasing errors from digitization.

The outputs from the lock-in amplifier 60 of FIG. 2 are input on lead 61, 63 to a multi-channel digitizer 64. After digitization, the data is transferred from digitizer 64 to a computer 66 for storage and analysis.

Figure 5:
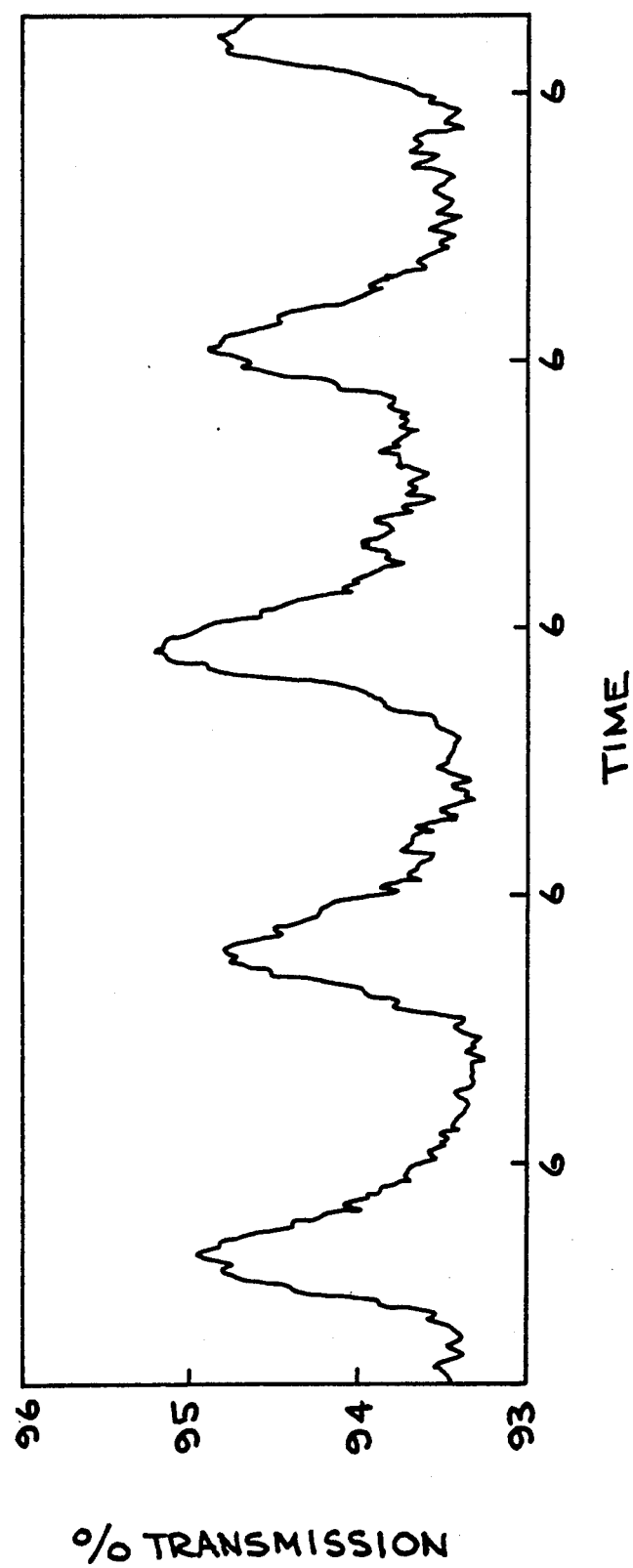
FIG. 5 depicts an example of processed data in a transmission versus time format according to the present invention.

FIG. 5 depicts an example of processed data according to the present invention in a transmission versus time format. The data in FIG. 5 is the result of 128 averages by digitizer 64 of FIG. 2, and has been normalized by the reference signal and the 100% transmission data. These results imply that the diagnostic system according to the present invention is capable of measuring transmission changes of 0.1% to 0.2%.

The foregoing description of the preferred embodiment of the present invention has been presented for purposes of illustration and description. It is not intended to be exhaustive or to limit the invention to the precise form disclosed, and many modifications and variations are possible in light of the above teaching. The preferred embodiment was chosen and described in order to best explain the principles of the invention and its practical applications to thereby enable others skilled in the art to best utilize the invention and various embodiments and with various modifications as are suited to the particular use contemplated. It is intended that the scope of the invention be defined only by the claims appended thereto.

What is claimed is:

1. A high bandwidth atomic vapor density diagnostic system comprising
    means for generating a high bandwidth laser beam,
    means for amplitude modulating said high bandwidth laser beam,
    means for propagating the modulated laser beam through an atomic vapor during one or more photoionization events,
    means for detecting the propagated laser beam to form a detected signal, and
    lock-in amplifier means for removing pickup noise from said detected signal.

2. A system as in claim 1 including
    means for generating a first acousto-optic carrier reference signal, means for generating a second higher frequency carrier signal, acousto-optic driver means for modulating said second signal by said first signal resulting in a sinusoidal carrier signal, and acousto-optic modulator means for modulating said laser beam with said sinusoidal carrier signal to form said modulated laser beam.

3. A system as in claim 2 wherein said modulating means includes means for generating a local oscillator reference signal.

4. A system as in claim 1 including a single mode fiber optic means for transporting said modulated laser beam to a remote location to form a transported modulated laser beam.

5. A system as in claim 1 including reference detector means for detecting said transported modulated laser beam.

6. A system as in claim 1 wherein said lock-in amplifier means includes means for removing out of band noise signals from said detector signal.

7. A system as in claim 6 wherein said lock-in amplifier means include means for removing out of phase pickup noise from said detected signal.

8. A system as in claim 1 including means for digitizing said detected signal.

9. A system as in claim 8 including means for processing said digitized signal to measure the vapor density variation during one or more of said single photoionization events.

10. A high bandwidth atomic vapor density diagnostic system comprising means for generating a high bandwidth laser beam,
means for amplitude modulating said high bandwidth laser beam to form a sinusoidally modulated laser beam,
means for propagating said sinusoidally modulated laser beam through an atomic vapor during one or more photoionization events,
detector means for detecting the propagated signal,
lock-in amplifier means for removing pickup noise from said detected signal,
means for digitizing said detected signal, and
means for measuring the vapor density variation of said atomic vapor over one or more of said photoionization events.

11. A high bandwidth atomic vapor density diagnostic system comprising means for propagating a low power amplitude modulated laser beam through an atomic vapor during one or more photoionization events, and
means for measuring the vapor density variation of said atomic vapor over one or more of said photoionization events.

12. In a high bandwidth vapor density diagnostic system, the method comprising the steps of amplitude modulating a high bandwidth laser beam,
propagating the modulated laser beam through an atomic vapor during one or more photoionization events,
detecting the propagated laser beam, and
removing pickup noise from the detected signal.

13. In a high bandwidth atomic vapor density diagnostic system, the method comprising the steps of generating a high bandwidth laser beam,
amplitude modulating said high bandwidth laser beam to form a sinusoidally modulated high bandwidth laser beam,
propagating said sinusoidally modulated laser beam through an atomic vapor during one or more photoionization events,
detecting the propagated signal,
removing pickup noise from said detected signal,
digitizing said detected signal, and
measuring the vapor density variation of said atomic vapor over one or more of said photoionization events.

14. In a high bandwidth atomic vapor density diagnostic system, the method comprising the steps of propagating a low power high bandwidth amplitude modulated laser beam through an atomic vapor during one or more photoionization events, and
measuring the vapor density variation of said atomic vapor over one or more of said photoionization events.

* * * * *